United States Patent [19]

Hoffman et al.

[11] 4,072,041
[45] Feb. 7, 1978

[54] SHORT-CRIMP SURGICAL NEEDLE

[75] Inventors: John Ronald Hoffman, New Milford; Peter John Marsland, Monroe, both of Conn.

[73] Assignee: American Cyanamid Company, Stamford, Conn.

[21] Appl. No.: 751,768

[22] Filed: Dec. 16, 1976

Related U.S. Application Data

[62] Division of Ser. No. 691,102, May 28, 1976.

[51] Int. Cl.² ........................................... B21D 37/10
[52] U.S. Cl. ................................. 72/416; 29/517; 72/470; 128/339; 163/1; 163/5
[58] Field of Search ................ 72/416, 409, 410, 415, 72/412, 470, 474; 128/339, 335.5; 163/1, 5

[56] References Cited

U.S. PATENT DOCUMENTS

| | | | |
|---|---|---|---|
| 2,272,244 | 2/1942 | Klein | 29/517 |
| 2,533,943 | 12/1950 | Klein | 72/453.01 |
| 3,611,551 | 10/1971 | Shave | 128/339 |
| 3,910,282 | 10/1975 | Messer | 128/339 |
| 3,980,177 | 9/1976 | McGregor | 128/335.5 |

FOREIGN PATENT DOCUMENTS 2,459,696  10/1975  Germany ......................... 128/339

Primary Examiner—C.W. Lanham
Assistant Examiner—Gene P. Crosby
Attorney, Agent, or Firm—Charles F. Costello, Jr.

[57] ABSTRACT

Surgical needles are attached to sutures with controlled pull-out characteristics by a short crimp—that is a crimp whose length is markedly less than the length of the end of the suture in the needle; with an essentially undistorted portion of the needle adjacent to where the suture emerges from the needle, and an essentially undistorted portion around the front of the suture, so that only a short section of the needle is crimped around the suture. This leaves the suture uncrushed where it emerges from the needle and hence of superior strength where sharp bends occur during use. It also leaves an undistorted portion of the suture ahead of the crimp so that on pull-out, the suture is retained not only by frictional engagement of the crimp but also by the forces required for the distortion of the head of the suture so that it will pull through the reduced section of the crimp.

1 Claim, 16 Drawing Figures

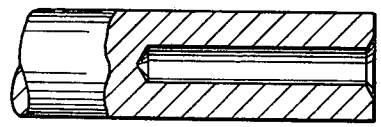
FIG. 8
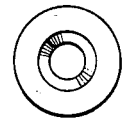
FIG. 9
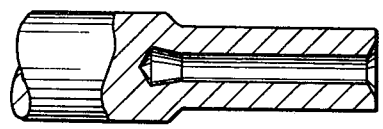
PRIOR ART
FIG. 10
FIG. 11
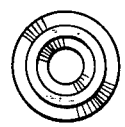
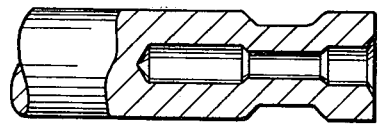
SHORT CRIMP
FIG. 12
FIG. 13
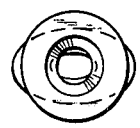
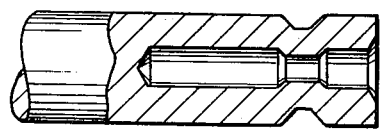
VERY SHORT CRIMP
FIG. 14
FIG. 15
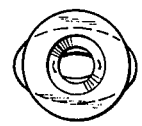
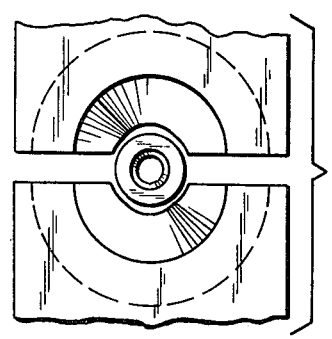
FIG. 16

SHORT-CRIMP SURGICAL NEEDLE

This is a division of application Ser. No. 691,102 filed May 28, 1976.

BACKGROUND OF THE INVENTION

The attachment of surgical needles to surgical sutures is a mechanical problem which is most challenging. If an eye is used, so that the thread is doubled through the eye of a needle, as in conventional sewing, the doubled end of the suture in the eye must pass through tissues during use, which enlarges the suture hole in tissue leading towards loss of liquid tightness, and increased trauma.

There has long been a trend towards eyeless needles in which the end of the suture is fixed to the needle so that the suture is pulled axially through the tissue causing a minimum of trauma. Preferably, it is desirable that the needle have a diameter that is only slightly larger than the suture. The attachment must be one which (a) is predictably secure, (b) causes a minimum of damage to tissue, (c) is convenient for the using surgeon, (d) permits sterilization and (e) entails reasonable costs, so that the suture needle may be attached economically. The attachment must stand up under the rigors of manufacture, sterilization, storage and shipment and use.

Rethreadable needles have many theoretical advantages, such as permitting reuse of the needle to avoid the cost of a new needle for each suture and because of such reuse can have a more expensive quality of steel and a more expensive quality of point than a disposable needle. However, any reusable needle requires some system for attaching the suture to the needle which permits reloading of a suture in the needle either in the operating room by operating personnel under sterile conditions or outside of the operating room under conditions which permits cleaning and sterilization of the needle, coordinated with the attachment of the suture, under such conditions that the final product is clean, sterile, and readily stored between the time of reloading and the time of use. With requirements for sterility, low cost, convenience and a minimum of size of the attachment system to avoid an unduly large surgical needle hole in tissue and a desirably smooth exterior so that the needle will slide through the tissue with a minimum of damage, so many conflicting requirements are presented that reloadable low trauma needles are not in common use.

The most common type of surgical needle is a single use needle of appropriate size and shape which is crimped to the end of the suture, so that the needle is used but once and then discarded. The attachment can be either a "drilled end" needle, that is one in which a concentric hole is formed in the end of the needle in which the suture is placed and the needle crimped around the suture; or a "flange" needle in which a U-shaped channel is stamped into the end of the needle with the ends of the U being crimped about the suture to hold the suture.

In either system, the crimp must be strong enough so that the suture remains attached to the needle during the placement of the needle and the attached suture through tissues. After the suture is placed in the tissues, it is frequently convenient to detach the needle so that at an appropriate time in the surgical procedure the ends of the suture can be tied together without the needle dangling around to stick or cut the patient, surgeon or nurse. Cutting of the suture with scissors or a scapel is a convenient method of disengaging the needle but requires an extra instrument and an extra manipulation. It would seem particularly convenient to pull the needle from the suture if the attachment of the needle to the suture is such that convenient disengagement may occur. Some surgeons have used such techniques with standard needles having pull-off values in conformity with U.S. Pharmacopeia requirements.

The pull required for pulling the needle off the suture or breaking the suture is referred to in the U.S. Pharmacopeia as needle attachment, or testing the security of attachment of eyeless needles to sutures. For convenience the term pull-off is herein used, as the present invention is to permit the control of pull-off to desired limits—often well below the breaking strength of the suture on either straight pull or knot pull.

Needles have been suggested in which from either a cutting edge in the needle, or the firmness of attachment, the needle can be detached from the suture at a reasonably predictable value which is acceptable.

The problem is that the pull-off must be at a sufficiently high value that the suture may be placed without risk of the needle becoming detached from the suture during placement; and yet it must pull-off at a value sufficiently far below the breaking strength of the suture that the needle will predictably pull-off before the suture breaks, and additionally must pull-off at a value which is reasonably exertable upon the needle by the surgeon at the time of use.

These theoretical objectives are difficult to obtain in practice. Manufacturing tolerances for the needle and the suture are such that a predictable acceptable pull-off value has been difficult to achieve under commercially practical manufacturing practices, so that firm competent attachment at U.S. Pharmacopeia standards has been usual.

For instance, whereas the wire size from which needles are made may vary in the order of a thousandths of an inch between lots, it is difficult to hold the outside diameter of the needle to less than plus or minus about two tenthousandths in a single lot. It is difficult in production to drill or otherwise form a hole with less than a variation of plus or minus another two tenthousandths of an inch.

The braid size of a suture always varies somewhat. Additionally, to aid in insertion in the needles it is conventional practice to end-dip. Sutures stock is wrapped on a frame under a comparatively uniform starting tension. However, the frame distorts from the large numbers of turns of suture strand under tension placed on the frame, and as the frame is strained, the tension on the initial turns of suture tends to be reduced.

Additionally variations in the coating material, the time and concentration of the bath and drying conditions are such that the end-dipped size may vary in the order of about a thousandth of an inch within a single production run.

Conventional crimp operations are difficult to control. Usually crimp is between dies that close to a fixed gap, and any variation in the crimp dies, the needle size, the hole size and the suture size changes the degree of crimp, and the change can be larger than is acceptable in trying to manufacture a controlled release or controlled pull-off suture-needle combination. Quality control is difficult.

Other approaches such as crimping to a controlled pressure, or using a combined pressure and gap cycle have been considered. The usual approach is to increase the degree of crimp until the crimping shears off the suture on a test sample, then back off on the degree of crimp until the sutures are not sheared off, and pull-off above USP limits, and after testing a representative group of sutures, proceeding to production.

In many instances each suture is non-destructively tested to a minimum pull-off value in routine production. Only those that pass a test load are accepted for further processing.

In addition to size effects, the surface smoothness of the suture and the needle hole, and lubricants on either affect the pull-off values. Some needles are lubricated with a silicone or polytetrafluoroethylene to reduce tissue drag in use. The needle hole can be filled with xylene or other volatile solvent during coating to reduce the penetration of the lubricant into the needle-hole.

In theory, if all process parameters are perfectly controlled, replicate results are obtained. In practice, so many factors enter that adequate control in production is easier to describe than accomplish.

PRIOR ART

U.S. Pat. No. 86,769 — Marriott — Feb. 9, 1869 — "Improvement in Needles" shows a eyed needle in which the eye has a cutting-edge in the eye to cut the thread without resorting to a knife. The needle is primarily used for sewing canvas.

U.S. Pat. No. 1,981,651 — Logan — Nov. 20, 1934 — "Surgical Needle and Suture" shows an eyeless surgical needle having a male threaded end on which is screwed a tube like sleeve, with a reduced exit diameter, so that a suture with a knot or enlarged end can be threaded through the sleeve and the sleeve screwed on the needle. The sleeve is unscrewed and reloaded for subsequent sutures.

U.S. Pat. No. 2,014,170 — Everett — Sept. 10, 1935 — "Surgical Suture and Needle" shows an eyeless rethreadable needle having a channel with an enlarged mouth and undercut sides, into which a knotless stop on the end of the suture is fitted. After stitching, the end of the suture is detached by backing out, and the needle reused.

U.S. Pat. No. 2,240,330 — Flagg and Reese — Apr. 29, 1941 — "Surgical Needle or the Like", shows an eyeless surgical needle having a shank on the butt end of the needle, and a suture having a sleeve on its end, which sleeve removably fits over the shank. A pawl on the sleeve fits in a notch in the shank so that on relative rotation, the suture is readily detached, and the needle reused. The slipping off of eyed needle is shown.

U.S. Pat. No. 2,411,079 — Baule — Nov. 12, 1946 — "Method of Attaching Sutures to Shanks of Surgeon's Needles" shows a single use needle which is expanded at the butt, drilled, and after insertion of the suture, the expanded portion is contracted so that its external diameter is about that of the body of the needle and the internal diameter grips the suture with a headed portion of the suture beyond the contracted portion, serving to retain the suture. A conical entrance to the base is provided to partially relieve breaking strains. The assembly is concentric. No pull-off estimates are given.

U.S. Pat. No. 2,728,343 — Everett — Dec. 27, 1955 — "Sewing Needle" shows a multiple indentation crimp; in column 1, line 36 "Preferably the joint between the ligature and needle should have a tensile strength of about half the ultimate tensile strength of the ligature,--". This patent shows a crimping machine with a series of five teeth to make five indentations—with the smallest indentation nearest the butt end of the needle.

U.S. Pat. No. 3,074,409 — Bielz — Jan. 22, 1963 — "Surgical Needle for Medical Purposes" shows a slitted pull-out needle in which the suture is retained in an open spring groove so that "After the sewing operation has been completed, it is merely necessary to exert a strong pull in the direction of the needle axis on the thread portion protruding from the needle end in order to completely remove the thread from the needle whereupon the latter can be used for further sewing operations."

U.S. Pat. No. 3,736,646 — Schmitt and Epstein — June 5, 1973 — (filed Oct. 18, 1971) "Method of Attaching Surgical Needles to Multifilament Polyglycolic Acid Absorbable Sutures" column 16, line 48 and following discloses as conventional the use of nylon in isopropanol for end-dipping braided sutures stretch wrapped around parallel bars, so the stretched filamentary material is cut clean without an accumulation of resin. This patent claims the use of 15%-85% to 85%-15% glycolic acid lactic acid copolymers for end-dipping.

U.S. Pat. No. 3,799,169 — Beroff and Ferguson — Mar. 26, 1974 "Lateral Release Suture" shows a controlled release needle-suture combination with the suture adhesively united to a channel in the needle, with a lateral pull for release. This patent points out with reference to the parent application of McGregor the very narrow quality control limits required for manufacturing a controlled release of the swaged type to get acceptable release limits (col. 1, lines 22-41).

U.S. Pat. No. 3,890,975 — McGregor — June 24, 1975 (C-I-P of Ser. No. 258,159, filed May 31, 1972) "Controlled Release Suture" shows resin end-dipped braided and monofilament sutures swaged to compress the end of the needle holding the suture between flat dies to compress the suture to between 62% and 75% of its original diameter, with a pull-out of 3 to 26 ounces.

U.S. Pat. No. 3,875,946 — Duncan — Apr. 8, 1975 — "Controlled Release Suture" shows a release control by pre-stressing and partially pulling the suture out of the needle until the pull force drops to a desired value. Pull out values are claimed of:

| Suture Size | Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 and larger | 10-26 |

U.S. Pat. No. 3,892,240 — Park — July 1, 1975 — "Surgical Needle Apparatus" shows a pull-off needle having a partial axial bore, and a frictionally engaged snap slot, and teaches a sharp tug to disengage after passage through tissue. (Col. 1, lines 62-63).

U.S. Pat. No. 3,924,630 — Walldorf — Dec. 9, 1975 — "Manufacture of Controlled Release Fluid Swellable Sutures" shows a suture swollen in the drilled end swaged recess so that a pull-out of 3 to 26 ounces is obtained.

U.S. Pat. No. 3,926,194 — Greenberg & Quade — Dec. 16, 1975 — "Sutures with Reduced Diameter at Suture Tip" shows reducing the diameter of the suture at the end of attachment to the suture so that the residual strength is within desired pull-off limits.

U.S. Pat. No. 3,943,933 — Gertzman — Mar. 16, 1976 — "Suture with Radiation Degradation Near Needle-Suture Junction" shows a section of the suture adjacent to the needle which is weakened by radiation to give a breaking strength of 3 to 26 ounces.

U.S. Pat. No. 3,949,756 — Ace — Apr. 13, 1976 — "Sutures with Notch Near Needle-Suture Junction" shows a suture weakened by a notch near the attachment to the needle so that the breaking strength is from 3 to 26 ounces.

SUMMARY OF THE INVENTION

It has now been found that the pull-out characteristics of a surgical suture in a surgical needle can be controlled by using a short crimp. A short crimp is one in which the crimped portion of the needle is less than the length of the suture end which is inserted in the needle so that there is both a short uncrimped section behind the crimp and an uncrimped section ahead of the crimp with only a comparatively short section of the needle crimped about the suture at a section behind the front end of the suture. This means that the uncrimped end of the suture must be pulled through the crimp; and reduced in diameter or flattened as it is pulled through the crimp. By requiring such distortion as the end of the suture is pulled through the crimp, as well as the friction of the suture in the crimp, it is practical to achieve consistent crimp retention or pull-out values which permit the needle to be pulled from the suture by the surgeon at the time of use. Critically importantly, the short crimp permits values within an acceptable pull-off range to be achieved using practical commercial tolerances in manufacturing procedures.

In theory, the friction between two surfaces is the product of the coefficient of friction times the loading normal to the surfaces. The loading is the unit load times the area. In the attachment of sutures to needles by crimping, the coefficient of friction is affected by surface smoothness, the materials of construction, and lubricants, or coating materials. The loading is critically affected by the area of crimp because the suture is deformed beyond its elastic limit into the plastic range. The short crimp reduces the length of crimp, and hence its area so that when stressed to the limit, the pull-out values are reduced—and more importantly are more consistent. The maximum loading is the plastic flow limit of the resin dipped end of the suture times its area.

Also with a short crimp, the crimp tends to be deeper for a given pull-out value. Variations from tolerances in needle outside diameter (wire size), needle hole size and suture diameter all are cumulative as the swaging dies close to a fixed dimension. With a shallow crimp, this cumulative tolerance is larger with respect to the depth of crimp. With a deeper crimp, the proportion becomes less.

Obviously, there are manufacturing tolerances set on, and necessarily variations in, the diameter of the exterior of the needle, the size of the drilled hole in the needle, and perhaps larger variations in the size of the dipped-end of the suture to be inserted in the blind hole in the surgical needle. In a manufacturing process, it is not practical to make separate measurements on each individual suture and each needle before they are assembled, and then modify the degree of crimp for these particular measurements. Instead it is necessary to set the swaging dies used to crimp the suture into the needle for a series to be run successively with the same swage die setting. In practice it is customary to change the degree of crimp until a desired pull-out value is obtained, and then use the same swaging dies setting on a production run, with adjustments made if pull-out values get out of control. The more exotic aspects of crimping to a particular value by using dies with a specified closing strength, or having a cycle in which both the position and closing force are measured and modified to accomodate variations in needle and suture size present complications which add to the cost of production, and are not required for high quality commercial production of sutures using the present invention.

It is found that the setting of the die to a gap which is controlled by experience in a run, is economical, and gives pull-out values which are within a desired range—without measuring the actual gap.

For a suture needle combination in which the needle is to be detached by snapping off or pulling off the needle at the time of placement, it is necessary that the suture be sufficiently firmly attached to the needle that in the stitching operation or placement of the suture the suture does not accidentally fall off the needle. In sewing through tissue the suture remains attached to the needle. This value should be at least 0.4 pounds for size 3/0 or larger, it should be at least 0.25 pounds for size 4/0 and may be taken as 0.1 times the breaking strength of the suture for sizes 5/0 and smaller. The minimum can effectively be controlled as the average pull-out minus 2 sigma where sigma is the standard deviation.

It is practical in production to run a minimum pull-out value on the attachment of needles to each suture. If the pull-out is too low, the product is not satisfactory, and if it is above a minimum value there is no destruction. Aside from statistical variations in pull-out, there are occasional non-statistical errors introduced such as a failure by the operator to bottom the end of the suture in the drilled hole in the needle, or some mechanical failure such as a spur in the needle hole or a defective cut on the end of the suture which prevents full insertion of the suture into the needle hole. a skilled operator will frequently detect flaws that would induce such errors, but it is convenient and feasible to run a quality control test on a large number of even all sutures needled to be sure that the minimum attachment values are reached.

The maximum value for the pull-out is more difficult to control. A value of about 3 pounds for size 0 and larger, about 2½ pounds for 2/0 and 3/0, and about 1½ pounds for size 4/0 and smaller, or half the tensile strength of the suture whichever is smaller, is a practical value.

If pull-out is over 2½ pounds for sizes 3/0 and 2/0 or 3 pounds for sizes 0 and 1, particularly with the larger needle sizes, it may become difficult for the surgeon to pull the needle off the suture, or to hold the suture while pulling off the needle.

From the production standpoint, it is feasible to test the maximum pull-off value on only representative samples, because the test is destructive and the samples are discarded after testing.

By measuring the average pull-out for a group of needles and then calculating the standard deviation (sigma) and doubling the standard deviation and adding and substracting to the average, values are obtained which represent the limit within which 95% of the sutures can be expected to fall.

For random errors, 95% can be expected to be within plus or minus 2 standard deviations of average and 99.5% can be expected to be within 3 sigma of average.

The present short crimp permits production of commercial quality needled sutures from commercial quality needles and end-dipped sutures within a range such that 95% are easily within the desired values and usually 3 sigma values are also within these desired limits. There is a possible exception in minimum pull-out values, which result from manufacturing defects which are not random errors, and by testing are discarded.

Variations in suture size, the needle size, the depths of holes drilled in the drill-end needles, and many other factors can enter. Minor variations in one of these variables can be compensated by changes in others. Hence, arbitrary standards should not be set on other than quality of the product. It must be considered that in countries other than the United States the suture sizes may be different, so comparable limits may be established based on suture sizes used in such countries.

It is found in the United States that the most common needle and suture sizes may well be within the following ranges:

TABLE 1
NEEDLE DIMENSIONS

| Suture Size Designation | USP XIX - Nonabsorbable Suture Diameter | | Typical Needle Diameter | Typical Hole Diameter thousands* of an | Typical Hole Depth | Typical crimp |
|---|---|---|---|---|---|---|
| | mm | inches | Inches | inch (mils) | Inches | Length - inch |
| 6-0 | 0.070–0.099 | 0.0026–0.0039 | 0.013 | 6.4–7.0 | 0.030 | 0.010 |
| 5-0 | 0.10 –0.149 | 0.0039–0.0059 | 0.015 | 8.8–9.6 | 0.035 | 0.010 |
| 4-0 | 0.15 –0.199 | 0.0059–0.0078 | 0.017 0.022 | 10.2–11.0 | 0.042 | 0.012 |
| 3-0 | 0.20 –0.249 | 0.0079–0.0098 | 0.024 0.039 | 12.5–13.5 | 0.050 | 0.012 |
| 2-0 | 0.30 –0.339 | 0.0118–0.0133 | 0.026 0.039 0.050 | 15.2–16.2 | 0.057 | 0.012 |
| 1-0 | 0.35 –0.399 | 0.0138–0.0157 | 0.039 0.044 0.050 | 18.2–19.2 | 0.060 | 0.012 |
| 1 | 0.40 –0.499 | 0.0157–0.0196 | 0.039 0.044 0.050 | 21.2–22.2 | 0.070 | 0.012 |

*Hole size tolerance in a single lot is 0.2 mils. All crimps inset 0.010 inch from blunt end of suture USP XIX has slightly different sizes of sutures for collagen sutures and a third set of sizes for synthetic absorbable sutures. Size designations extend from size 10-0 to size 7. This table shows the more commonly used sizes. Comparable dimensions can be used for larger and smaller sizes. Note that the USP XIX sizes are by a specified bridged measurement. Optical size measurements of the suture, and the end-dipped portions may be different.

Other advantages and objects of the present invention are apparent from the following detailed description and drawings which are illustrative only and not the outer limits of the present invention.

In the drawings:

FIG. 8 is a sectional view of an uncrimped needle.

FIG. 9 is an axial view of a blunt end of the needle of FIG. 8.

FIG. 10 is a sectional view of the prior art crimped needle.

FIG. 11 is an axial view of the conventional crimped needle of FIG. 10.

FIG. 12 is a sectional view of a short crimp needle.

FIG. 13 is an axial end view of a blunt end of the short crimped needle of FIG. 12.

FIG. 14 is a sectional view of a very short crimped needle.

FIG. 15 is an axial view of a blunt end of the needle of FIG. 14.

FIG. 16 is a view of the end of the needle between the swaging dies with the swaging dies being shown in needle positioning relationship.

Figure 1:
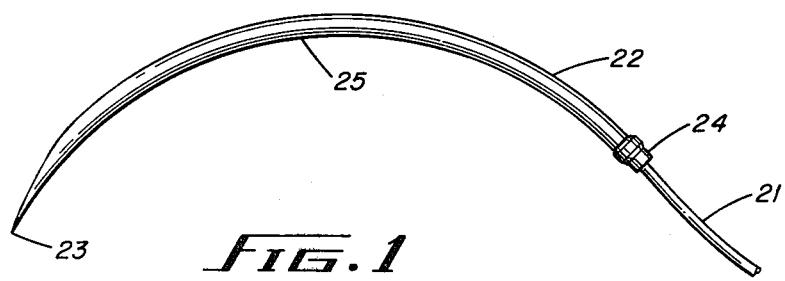
FIG. 1 shows a curved surgical needle to which is attached a surgical suture.

As shown in FIG. 1 a surgical suture 21 is crimped to an eyeless surgical needle 22. The eyeless surgical needle has a penetrating point 23 at the front end and has the surgical suture 21 crimped to the blunt end 24. The surgical needle itself may be of any of the conventional configurations such as straight or curved, and a conical point, a triangular point, cutting or reversed cutting, or a duck bill or spade point to meet with the preference of the using surgeon. The shank 25 may be round, slightly flattened, or with ridges or grooves to aid in gripping by needle forceps.

The surgical suture may be of any conventional suture material, braided, twisted or monofilament. Typical materials include silk, nylon, linen, cotton, polyethylene, polypropylene, natural materials such as catgut, and synthetic polymers having glycolic acid ester linkages subject to hydrolytic degradation to non-toxic, tissue compatible absorbable components, including polyglycolic acid.

When of braided or twisted construction it is preferred that the end of the suture, while under tension, be dipped into a plastic such as nylon in a volatile solvent, which solvent is permitted to evaporate and cause the filaments of the multifilament sutures to adhere to each other. By being under tension the diameter is a minimum, and tends towards rounder configuration. The end of the suture is cut, preferably at a slight angle such as 30°, with a very sharp knife or scissors so as to give a clean cut without distortion. Frequently a sharp powered rotary knife is used. It is important that the end of the suture be free from distortion as the suture is threaded into a small hole in the eyeless needle. A flattened or mutilated cut can so enlarge the end of a suture that it does not thread smoothly into the needle.

Figure 5:
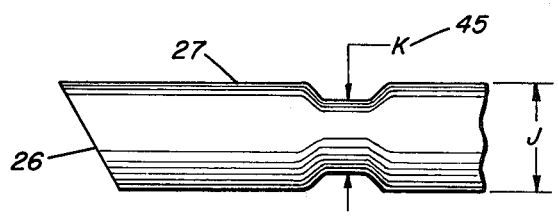
FIG. 5 is a side view showing the short crimped portion of the suture.

The end of a suture, as shown in FIG. 5, has a beveled cut 26 so that the end of the suture 27 is undistorted. Such end dipping and cutting has long been conventional in the industry, as mentioned in U.S. Pat. No. 3,736,646, supra, (Col. 16, lines 43–62) and in more detail in British patent specification No. 1,428,560.

Figure 4:
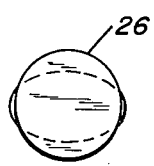
FIG. 4 is the axial view of the front end of a suture showing the undistorted front end and the elliptically compressed portion held in the short crimp.

FIGS. 4 and 5 as well as the other figures in the drawings are much enlarged to show details.

Table 1 above shows the sizes of needles and sutures that are in most common surgical use in the United States at the present time. For size 6/0 to size 1 sutures, the needle diameters are from about 0.050 inch to 0.013 inch. The needle diameter is sometimes called the wire diameter, being the diameter of the wire from which the needle is manufactured. The sutures fit into a needle hole 28 that has an inside diameter from about 0.0222 inch to 0.0064 inch. It is to be understood that in some surgical procedures larger needles and larger sutures are used, particularly as retention sutures, and for some operations particularly eye work or fine microscopic surgery, as for instance on the hands after injury, sutures and needles smaller than a 6/0 are used. The relative numbers of such sutures are small. The same proportions as disclosed for the present sutures can be used for either these larger or smaller sutures. Meticulous care is required in the manufacture of sutures smaller than 6/0 with magnifying lenses or low power microscopes being used for many of the operations. Techniques from the jewelers' trade in the manufacture and repair of small womens' watches may be adapted to the smaller sizes of sutures.

Figure 2:
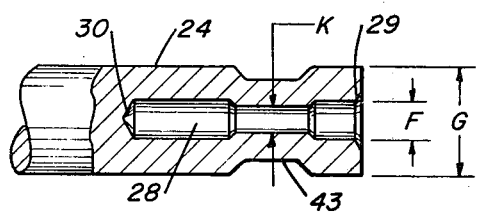
FIG. 2 is a cross sectional view of a surgical needle after being crimped.
Figure 3:
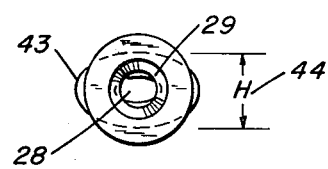
FIG. 3 is a axial view of the blunt end of the needle after being crimped.

The blunt end 24 of the needle 22 has therein a drilled hole 28. In the trade, the hole is referred to as a drilled hole even though it may have been made by the use of a laser beam or other technique. As shown in FIG. 2 and 3 a slight countersink 29 prevents a sharp corner being present at the exit from the drilled hole and aids in threading the suture into the drilled hole. The bottom end of the drilled hole may have a conventional slightly conical shape from the drilled point, here called a drill point of hole 30.

After insertion of the beveled cut 26 on the end of the suture 27 into the drill hole, the blunt end of the needle is crimped about the suture. The crimping is accomplished with swaging dies 31 shown in FIGS. 6, 7 and 16. The swaging dies preferably are of an extremely hard material such as tungsten carbide. The dies are symmetrical and conveniently have a rectangular cross section, which slide in ways. The ways are conventional and provide for moving the swaging dies 31 equally towards each other without lost motion.

Figure 6:
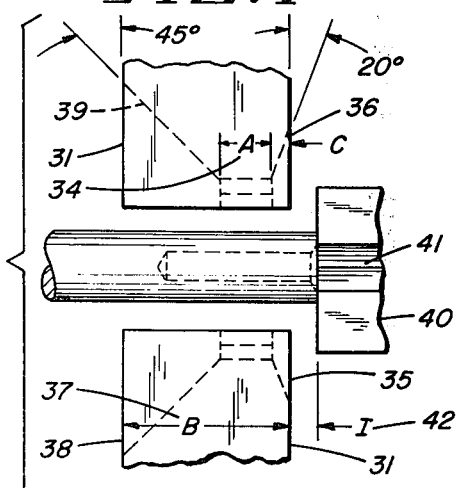
FIG. 6 is an exploded view of the swaging dies with a suture in position to be crimped against the threading block.

As shown in FIG. 6 the ends of the swaging dies when viewed in a direction parallel to the axis of the blunt end of the needle have a lap radius 32 designated $R_1$ the center of which is 0.0005 to 0.0015 inch outboard of the ends of the swaging dies, and which radius is slightly smaller than the radius of the surgical needle being crimped. This is called the lap radius 32. Near the lower ends of the lap radius 32 is an overlap radius 33 designated $R_2$. The center for the overlap radius 33 is approximately 0.004 to 0.009 inch outboard of the face of the swaging die. After roughing cuts these radiuses are readily accurately formed by fixing the dies in matched pairs the appropriate distance apart so that the centers for the lap radius or overlap radius coincide for the pair of dies, and then a cylindrical lap of the appropriate size coated with a fine lapping compound is used to lap the surfaces to the exact dimension with a very smooth surface.

When viewed as shown in FIG. 6 at right angles to the axis of the needle being swaged, the lap radius and overlap radius extend for the width of the swags die land 34 as shown by dimension A. At the exit face 35 of the die, the land is cut back at an angle of 20° with the length of the die and is inset for a die relief 36 as shown at C. A die relief of 0.010 inch is preferred. The swags die body width 37 is designated by the dimension B. At the entrance face 38 the die is cut away at an angle of 45° with the swage die land 34. The thus formed entrance cone 39 has a dual function of providing reinforcement for the swage die land, and serving as a guide for the insertion of the blunt end of the surgical needle between dies.

Figure 7:
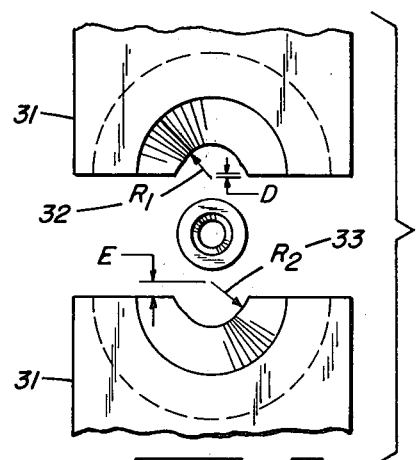
FIG. 7 is an exploded axial view of the needle and the swaging dies.

The dies in FIG. 6 and 7 are shown in exploded position to permit clear illustration of their construction. The dies in use are shown in FIG. 16. The dies are separated just enough so that the blunt end 24 of the needle may be slipped between the dies 31. The dies open just enough so that the lands 34 holds the surgical needle in approximately axial position with a minimum of free play. This causes the surgical needle, when inserted, to be held in a relatively fixed position. The suture is fixed laterally by a threading block 40. The threading block has therein a threading groove 41, conveniently a 90° V-groove, with the block and the threading groove being so positioned that a suture placed in the threading groove is aligned with the drilled hole in the surgical needle 22 between the swaging dies 31. The threading block is placed either in contact with the exit face 35 of the swaging dies or is spaced a stop clearance dimension 42, shown at I from the exit face. When the blunt end of the needle is placed between the swaging dies, and in contact with the face of the threading block, alignment for both suture insertion and swaging is provided.

The suture is inserted into the drilled hole until it bottoms on the bottom of the drilled hole, then the swaging dies are compressed to crimp the needle on the end of the suture. As shown in FIG. 3 the needle is compressed into an approximately elliptical configuration with small portions of the metal being displaced into the overlap radius of the swaging dies, to form a minimum cross section of the swaged needle 44 as shown by the letter H. Compressing the outside of the needle to the minimum cross section in turn compresses the suture inside the drilled hole to a compressed suture thickness 45 shown as dimension K as shown in FIG. 5.

In commercial practice, the actual measurement of the minimum cross section dimension for the swaged needle barrel and its corresponding compressing of the suture thickness are difficult to measure and are of minimum significance. The truly significant value is the pull-out of the suture. The pull-out is measured on representative sutures and the closing of the swaging dies is changed by increasing or decreasing the closing of the dies on the needle until the desired pull-out value is obtained. In conventional crimping machines for swaging sutures into needles, either an over center toggle or eccentric cams are used to force the swaging dies towards each other. Finely threaded set screws are used to change this dimension in small increments.

In FIG. 8 and 9 is diagrammatically shown the blunt end of an uncrimped surgical needle. In FIG. 10 and 11 is shown the prior art crimp in which the drilled end is crimped for substantially its full length with a cylindrical crimp about the suture. Usually a double closing of dies is required to give such a round crimp. In such conventional crimp, the end of the suture is held by friction only and because of manufacturing variations, must be held tightly to insure that the minimum pull-out value is adequate. Compare the U.S. Pharmocopeia values on average and individual needle attachment or pull-out.

Similarly, the short crimp of the present invention is shown in FIG. 12 and 13, with the crimp being oval. A single closing of the swaging dies forms the crimp. The crimp leaves space for a head on the end of the suture, which head must be distorted as it is pulled through the oval of the crimp.

In FIG. 14 and 15 is shown a very short crimp which leaves a longer head on the suture. This crimp is about as short as can be obtained by production dies. Too thin a land is apt to cause an unacceptably high breakage rate. Any shorter crimp would be in effect cutting the end off the needle.

In the following examples are shown certain typical measurements, and certain typical values obtained in specific runs on sutures.

It is to be emphasized that much larger or much smaller needles and sutures than those shown in the examples can be used. The values are representative and in part show measurements made under laboratory conditions, with careful measurements of components before assembling. Other examples show results to be anticipated with production runs, using production variations in the sizes of needles and sutures, and without specific measurements being taken on individual needles.

In the following three examples, needles and sutures were carefully selected to maintain constant dimensions. Needle holes were gauged with pin gauges. Outside diameters of needles were measured with a micrometer, and the suture was measured optically to avoid distortion in the measurement operation. The following dimensions were kept constant.:

TABLE II

| Symbol inches | Description |
| --- | --- |
| B-0.094 | Swage Die Body Width |
| C-0.010 | Swage Die Relief Dimension |
| D-0.001 | Dimension from Swage Die Face to Lap Radius Center Line |
| E-0.009 | Dimension from Swage Die Face to Overlap Radius Center Line |
| $R_1$-0.017 | Lap Radius |
| $R_2$-0.022 | Overlap Radius |
| G-0.0392 | Needle Barrel Diameter |
| H-0.034 | Minimum Cross Section Dimension for Swaged Needle Barrel |

EXAMPLE 1

SIZE 2/0 SILK

A group of size 2/0 black braided silk sutures, the ends of which have been dipped in a nylon solution, were crimped in dies to the values shown in the table and the pull-off values measured:

EXAMPLE NO. 1

| | | SIZE 2/0 BLACK BRAIDED SILK | | | | |
| --- | --- | --- | --- | --- | --- | --- |
| Die No. | Swage Die Land Width Inches (A) | Needle Hole Diameter (Inches) (F) | Suture Diameter (Inches) (J) | Suture Compression (Inches) (K) | Stop Dimension (Inches) (I) | Pull-Off (lbs) |
| #1 | .030 | .0159 | .0138 | .0107 | .000 | 2.80 |
| #1 | .030 | " | " | " | .015 | 2.40 |
| #2 | .020 | " | " | " | .000 | 2.40 |
| #2 | .020 | " | " | " | .015 | 1.70 |
| #3 | .010 | " | " | " | .000 | .65 |
| #3 | .010 | " | " | " | .015 | .15 |

The additional distance for the stop dimension, needles in which the distance between the back end of the crimp and the back end of the needle was increased caused a reduction in pull-off strength. by having the exit face of the swaging die against the face of the treading block, consistent useful results are obtained.

EXAMPLE 2

SIZE 2/0 NYLON

A similar run was made using size 2/0 braided nylon which had been end dipped in a nylon solution showed the following values:

EXAMPLE NO. 2

| | | SIZE 2/0 BRAIDED NYLON | | | | |
| --- | --- | --- | --- | --- | --- | --- |
| Die No. | Swage Die Land Width Inches (A) | Needle Hole Diameter (Inches) (F) | Suture Diameter (Inches) (J) | Suture Compression (Inches) (K) | Stop Dimension (Inches) (I) | Pull-Off (lbs) |
| #1 | .030 | .0158 | .0150 | .0106 | .000 | 3.90 |
| #1 | .030 | " | " | " | .015 | 2.20 |
| #2 | .020 | " | " | " | .000 | 3.00 |
| #2 | .020 | " | " | " | .015 | 2.90 |
| #3 | .010 | " | " | " | .000 | .37 |
| #3 | .010 | " | " | " | .015 | .23 |

EXAMPLE 3

SIZE 2/0 POLYGLYCOLIC ACID

A similar run was made using size 2/0 braided polyglycolic acid sutures which have also been dipped in a nylon solution:

EXAMPLE NO. 3

SIZE 2/0 BRAIDED POLYGLYCOLIC ACID

| Die No. | Swage Die Land Width Inches (A) | Needle Hole Diameter (Inches) (F) | Suture Diameter (Inches) (J) | Suture Compression (Inches) (K) | Stop Dimension (Inches) (I) | Pull-Off (lbs) |
|---|---|---|---|---|---|---|
| #1 | .030 | .0158 | .0145 | .0106 | .000 | 3.70 |
| #1 | .030 | " | " | " | .015 | 2.65 |
| #2 | .020 | " | " | " | .000 | 1.70 |
| #2 | .020 | " | " | " | .015 | 2.55 |
| #3 | .010 | " | " | " | .000 | .60 |
| #3 | .010 | " | " | " | .015 | .20 |

These three examples show that a short crimp reduces a holding strength but more importantly, as shown in later examples permits more consistent values under production conditions.

In the following examples, of commercial size lots of about 10,000, the swage die land width is 0.012 inch, and the swage die relief is 0.010 inch.

The dies had dimensions as follows, in thousandth of an inch (mils):

| Wire Diameter G | Lap Radius $R_1$ | Overlap Radius $R_2$ | Lap Center Outboard D | Overlap Center Outboard E |
|---|---|---|---|---|
| 50 | 23.5 | 26.5 | 0.5 | 6.0 |
| 44 | 20.0 | 24.0 | 1.5 | 8.0 |
| 39 | 17.0 | 22.0 | 1.0 | 9.0 |
| 26 | 11.0 | 14.5 | 0.5 | 8.0 |
| 24 | 10.5 | 14.0 | 0.8 | 8.0 |
| 22 | 9.5 | 13.0 | 1.0 | 8.0 |
| 17 | 7.5 | 9.5 | 1.0 | 6.0 |
| 15 | 6.5 | 8.5 | 1.1 | 6.0 |
| 13 | 5.5 | 7.0 | 1.2 | 4.0 |

For production, the dies are pre-set during set-up to give minimum and maximum pull-off of about:

| SIZE | MIN. LBS. | MAX. LBS. |
|---|---|---|
| 1 | 0.50 | 2.00 |
| 1/0 | 0.50 | 2.00 |
| 2/0 | 0.50 | 2.00 |
| 3/0 | 0.40 | 1.75 |
| 4/0 | 0.25 | 1.50 |

In production, each needle is tested for a minimum pull-off of 0.25 lbs. for sizes larger than 3/0 and 0.10 lbs. for 4/0. Because of inertia effects in rapid testing these values are lower than the true pull-off.

Samples are taken during production by each operator to ensure that the swaging dies continue to remain within desired limits. As such testing is destructive, the number tested can be lower when a process seems to be in good control.

EXAMPLE 4

3/0 NYLON SUTURES

A group of braided nylon sutures size 3/0 were crimped in needles having an outside diameter of 0.024 inch, a drill hole of about 0.013 inch, a depth of about 0.050 inch, all being within commercial productive limits of about 0.0002, plus or minus on needle outside diameter and drill hole diameter within the lot. The sutures measured 0.247 mm., (0.0097 inch) by USP methods. The ends were nylon dipped. The needle pull-off values in pounds on 30 samples taken at random from a run of about 10,000 showed values of:

| | | |
|---|---|---|
| .65 | .70 | .80 |
| .95 | 1.2 | .85 |
| .85 | .70 | .65 |
| .55 | .75 | .95 |
| 1.0 | .90 | 1.3 |
| .75 | 1.0 | .95 |
| .60 | .80 | 1.1 |
| .60 | .70 | 1.1 |
| .95 | 1.0 | .80 |
| .80 | .80 | 1.1 |

For the 30 values, the average is 0.86 pounds, and the standard deviation (sigma) is 0.19. The average plus and minus 2 standard deviations is 0.48 to 1.2 pounds which is well within acceptable limits. All pull-off values were within the desired range of 0.4 lbs to 2.5 lbs.

EXAMPLE 5

4/0 NYLON SUTURES

A similar group of 4/0 braided nylon sutures were crimped on needles having an outside diameter of 0.017 inch, a drill hole of about 0.0106 inch, a depth of 0.042 inch, all within commercial tolerances, and a suture measuring 0.195 mm (0.0077 inch) by USP methods. The ends were nylon dipped. The needle pull-off values in pounds on 30 samples from a run of about 10,000 were:

| | | |
|---|---|---|
| .30 | 1.2 | .75 |
| .95 | .60 | .80 |
| .40 | .70 | .65 |
| .75 | .70 | .45 |
| .55 | 1.2 | .60 |
| .95 | .60 | .65 |
| .45 | 1.2 | .40 |
| .50 | .95 | .70 |
| .95 | .65 | .70 |
| .60 | .65 | .60 |

For the 30 values, the average is 0.75 pounds, and the standard deviation (sigma) is 0.24. The average plus and minus 2 standard deviations is 0.27 to 1.2 pounds which is well within acceptable limits. All pull-off values were within the desired range of 0.25 lbs. to 1.5 lbs.

EXAMPLE 6

2/0 NYLON SUTURES

Following the procedure of Example 4, about 10,000 needles were crimped on size 2/0 braided nylon sutures. The needle had a nominal outside diameter of 0.026 inch, a drill hole of 0.0157, and depths of 0.057 inch. The suture diameter USP was 0.324 mm (0.0128 inch).

The pull-off values on 30 samples were:

| | | |
|---|---|---|
| 1.0 | 1.0 | 1.0 |
| .95 | .90 | 1.5 |
| 1.2 | .90 | 1.0 |
| 1.0 | 1.0 | 1.0 |

| | | |
|---|---|---|
| 1.4 | .85 | .75 |
| 1.0 | .70 | 1.2 |
| 1.1 | .95 | 1.3 |
| 1.4 | .95 | 1.2 |
| 1.6 | .85 | 1.2 |
| 1.0 | 1.2 | 1.2 |

For the 30 values, the average is 1.1 pounds, and the standard deviation (sigma) is 0.24. The average plus and minus 2 standard deviations is 0.64 to 1.6 pounds which is well within acceptable limits. All pull-off values were within the desired range of 0.4 lbs to 2.5 lbs.

EXAMPLE 7

2/0 SILK SUTURES

Following the procedures of Example 4 needles were crimped to size 2/0 braided silk sutures. The needles had a nominal outside diameter of 0.026 inch, a drill hole diameter of 0.0157 inch, and depth of 0.057 inch. The USP suture diameter was 0.317 mm. (0.0125 inch).

The pull-off values on 30 samples were:

| | | |
|---|---|---|
| .80 | .95 | 1.1 |
| 1.0 | .85 | 1.1 |
| 1.4 | .70 | .70 |
| 1.6 | 1.2 | 1.2 |
| .80 | .85 | .90 |
| 1.3 | 1.0 | 1.1 |
| .90 | .75 | .75 |
| 1.2 | .95 | .95 |
| 2.2 | 1.0 | .80 |
| .95 | 1.0 | .20 |

For the 30 values, the average is 1.0 pounds, and the standard deviation (sigma) is 0.34. The average plus and minus 2 standard deviations is 0.33 to 1.7 pounds which is well acceptable limits. All pull-off values were within the desired range of 0.4 lbs. to 2.5 lbs.

EXAMPLE 8

1/0 POLYGLYCOLIC ACID SUTURES

Following the procedure of Example 4, needles were crimped to size 1/0 braided polyglycolic acid sutures. The needles had a nominal outside diameter of 0.039 inch, a drill hole diameter of 0.0187 inch, and depths of 0.060 inch. The USP suture diameter was 0.394 mm (0.0155 inch).

The pull-off on 35 samples were:

| | | |
|---|---|---|
| 1.3 | 1.3 | 1.2 |
| 1.1 | 1.3 | 1.6 |
| 1.3 | 1.2 | 1.6 |
| 1.1 | .95 | 1.7 |
| 1.4 | 1.3 | 1.0 |
| 1.1 | 1.4 | 1.0 |
| .75 | .9 | .75 |
| 1.0 | 1.3 | 1.2 |
| 1.0 | .95 | 1.4 |
| 1.0 | 2.0 | 2.2 |
| 1.4 | .95 | 1.1 |
| 1.8 | 1.4 | |

For the 35 values, the average is 1.3 pounds, and the standard deviation (sigma) is 0.32 pounds. The average plus and minus 2 standard deviations is 0.66 to 1.9 pounds which is well within acceptable limits. All pull-off values were within the desired range of 0.4 lbs. to 3 lbs.

The production size runs show comparative pull-off values are more consistent than obtainable with conventional crimps. The crimp can be tightened to give higher values, and by increasing the land width and the tightness of crimp, values above USP limits may readily be obtained. The examples show the obtaining of a readily detachable needle with remarkable consistency.

In production, it is customary to set the closing crimp of the dies by measuring the pull-out of individual test sutures to give values well within production limits, so that manufacturing tolerances in needle diameter, hole inside diameter, suture size, and crimp itself, on a single swaging machine, permit production within acceptable limits. Each swaging machine is set separately, and tests are made periodically to be sure the pull-out continues to be acceptable.

We claim:

1. A two-piece suymmetrical swaging die for swaging a narrow crimp in a surgical needle having a coaxial cylindrical blind hole in the blunt end to hold a surgical suture therein comprising: a swaging die having a land having a lap radius the center of which is about 0.0005 to 0.0015 inch outboard of the ends of said die, said lap radius being slightly less than the needle radius, said die having a width along the axis of the needle less than about half the blind hole depth, and an overlap radius the center of which is about 0.004 to 0.009 inch outboard of the face of said die to permit metal displacement.

* * * * *